(12) United States Patent
Rajagopalan et al.

(10) Patent No.: US 6,664,367 B1
(45) Date of Patent: Dec. 16, 2003

(54) STABLE ANALOGS OF BIOACTIVE PEPTIDES CONTAINING DISULFIDE LINKAGES

(75) Inventors: Raghavan Rajagopalan, Maryland Heights, MO (US); Ananthachari Srinivasan, St. Charles, MO (US); Leon R. Lyle, Webster Groves, MO (US)

(73) Assignee: Biosynthema, Inc., St. Louis, MO (US)

( * ) Notice: Subject to any disclaimer, the term of this patent is extended or adjusted under 35 U.S.C. 154(b) by 0 days.

(21) Appl. No.: 08/278,437

(22) Filed: Jul. 21, 1994

(51) Int. Cl.$^7$ .............................................. C07K 16/00
(52) U.S. Cl. ...................... 530/311; 530/402; 530/317; 514/3; 930/280
(58) Field of Search ................................ 530/311, 402, 530/317; 514/3; 930/280

(56) References Cited

U.S. PATENT DOCUMENTS

| | | | |
|---|---|---|---|
| 4,272,506 A | | 6/1981 | Schwarzberg |
| 5,225,180 A | * | 7/1993 | Dean et al. .................. 530/311 |
| 5,382,654 A | * | 1/1995 | Lyle et al. .................... 530/311 |
| 5,413,778 A | | 5/1995 | Kunkel et al. |
| 5,431,899 A | | 7/1995 | Redmond et al. |
| 5,439,792 A | * | 8/1995 | Blake et al. ................. 530/402 |

OTHER PUBLICATIONS

Fischman et al., J. Nucl. Med., vol. 34, No. 12 (1993) "A Ticket to Ride: Peptide Radiopharmaceuticals", pp 2253–2263.

Mather et al., Cell Biophysics, vol. 21 (1992) "Radiiolabeled Octreotide What Lessons for Antibody-Medicated Targeting?", pp 93–107.

Thakur et al., Symposium Abstracts, IXth International Symposium on Radiopharmaceutical Chemistry (1992) "Tc–99M Labeled Sandostatin: Preparation and Preliminary Evaluation", pp 365–366.

Edwards et al, BBRL, vol. 136, No. 2, pp. 730–736, (1986).*

Jost et al, Collection Gechoslov. Chem. Commun., vol. 36, pp. 234–245, (1971).*

Smith–Jones, IXeme Symp. Int'l. on Radiochemistry, pp. 422–423, (1992).*

Rivier et al, Journal of Medicinal Chemistry, vol. 18, No. 2, pp. 123–126, (1975).*

Garcia, PNAS, vol. 85, pp. 5688–5892, (Aug. 1988).*

Rivier et al, Rec. Progr. Horm. Res., vol. 31, pp. 369–371 (1975).*

Mather et al, Cell Biophysics, vol. 21, pp. 93–107, (1992).*

\* cited by examiner

*Primary Examiner*—T. D. Wessendorf
(74) *Attorney, Agent, or Firm*—Blackwell Sanders Peper Martin LLP (57) ABSTRACT

Stable analogs of cyclic peptides containing disulfide linkages are disclosed. The disulfide linkage is modified by one of four methods: (a) sulfide contraction, (b) isosteric substitution, (c) thioketal expansion, or (d) alkylation expansion. In sulfide contraction the disulfide bond (—S—S—) is replaced with a monosulfide bond (—S—) in which a bifunctional effector molecule, such as a ligand or chemotoxic agent, is bound to the new peptide linkage. In isosteric substitution, one sulfur atom is replaced with a carbon atom and at least one of the carbon atoms at the modified site is a bifunctional effector molecule. In thioketal expansion, an alkylidene unit (—$CR_1C_2$—) is inserted between the two sulfur atoms. In alkylation expansion, an alkyl moiety of from $C_2$ to $C_3$, is inserted between the two sulfur atoms.

10 Claims, 2 Drawing Sheets

STABLE ANALOGS OF BIOACTIVE PEPTIDES CONTAINING DISULFIDE LINKAGES

BACKGROUND OF THE INVENTION

1. Field of the Invention

This invention relates to conformationally and chemically stable analogs of bioactive peptides containing disulfide linkages. The present invention also relates to disulfide linkage analogs containing a bifunctional effector molecule, such as a bifunctional chelating agent, antineoplastic agent, enzyme, coenzyme, or chemotoxin, at the same site where the disulfide bond is modified.

2. Technology Background

There are many bioactive peptides containing disulfide linkages. Many naturally occurring cyclic (and conformationally restricted) peptides contain disulfide linkages. These disulfide bonds exist primarily to ensure conformational rigidity. Peptides containing disulfide bonds usually exist as 10 to 20 membered ring macrocycles, although much larger ring sizes are known and are common in large polypeptides or proteins. Such small cyclic peptides and small peptidomimetics are becoming extremely important in diagnosis and therapy. In particular, they are being actively considered in targeted delivery of radio- and chemotherapeutic agents. See, Fischman, A. J. et al., "A Ticket to Ride: Peptide Radiopharmaceuticals," *The Journal of Nuclear Medicine*, Vol. 34, No. 12, December 1993.

A major limitation of these disulfide bridges is their instability to even mild reducing conditions; destruction of the —S—S— bond usually destroys the bioactivity of the peptide. For instance, due to the use of reducing agents, such as stannous ions and dithionite, the radiolabeling conditions required to prepare radiopharmaceuticals often destroy disulfide linkages. Similarly, blood stream constituents can degrade disulfide bonds. To be used in diagnosis and therapy, it is often necessary to attach a bifunctional effector molecule, such as a bifunctional chelating agents capable of complexing diagnostically and therapeutically useful metal ions, antineoplastic agents, enzymes, coenzymes, or chemotoxins, to the peptide. In the past, EDTA-like bifunctional chelating agents bearing side chains containing amino and carboxylic groups have been incorporated into the amino or carboxy terminal ends of bioactive peptides. See, Warshawsky and coworkers, *J. Chem. Soc. Chem. Comm.*, 1133 (1985) and *Synthesis*, 825 (1989); *J. Chem. Soc., Perkin Trans. I.*, 59 (1984); Arya and Gariépy *Bioconjugate Chem.*, 2, 323 (1991).

Often the amino or carboxyl terminal of the peptide is required for biologically activity, so that conjugating a ligand to the terminal end of the peptide destroys the peptide's bioactivity. If the bioactivity of the peptide is destroyed, then the peptide subsequently labeled with a radioisotope will have little value in diagnostic or therapeutic application.

It, therefore, would be a significant advancement in the art to provide analogs of cyclic bioactive peptides containing disulfide linkages which have improved chemical and biological stability while substantially retaining the overall 3-dimensional peptide conformation and bioactivity. It would also be a significant advancement in the art to couple bifunctional effector molecules to such peptide analogs.

Such stable analogs of bioactive peptides are disclosed and claimed herein.

SUMMARY OF THE INVENTION

The present invention is directed to stable analogs of cyclic bioactive peptides containing disulfide linkages. According to the present invention, the —S—S— bond is modified by one of four methods: (a) sulfide contraction, (b) isosteric substitution, (c) thioketal expansion, or (d) alkylation expansion. These procedures are illustrated generally below:

Sulfide contraction according to the present invention is the replacement of the disulfide bond (—S—S—) with a monosulfide bond (—S—) in which a bifunctional effector molecule, such as a bifunctional chelate, antineoplastic agent, or chemotoxin, is bound to the new peptide at the modified site, as illustrated below:

Wherein at least one $R_1$ or $R_2$ is a bifunctional effector molecule and the other $R_1$ or $R_2$ is selected from H, alkyl, aryl, hydroxyalkyl, aminoalkyl, carboxyl, and carboxyalkyl in which the carbon containing portions contain from 1 to 10 carbon atoms.

Isosteric substitution as used herein is the replacement of one sulfur atom of the disulfide bond with a carbon atom. At least one of the carbon atoms in the modified site of the peptide bears a bifunctional effector molecule, as illustrated below:

Wherein at least one $R_3$, $R_4$, or $R_5$ is a bifunctional effector molecule and the other $R_3$, $R_4$, or $R_5$ is selected from H, alkyl, aryl, hydroxyalkyl, aminoalkyl, carboxyl, and carboxyalkyl in which the carbon containing portions contain from 1 to 10 carbon atoms.

Thioketal expansion according to the present invention involves inserting an alkylidene unit (—$CR_6R_7$—) between the two sulfur atoms. Thioketal expansion can be accomplished by reduction followed by reaction of the resulting dithiol with aldehydes or ketones as follows:

where $R_6$ and $R_7$ may be the same or different and are selected from hydrogen, alkyl, aryl, hydroxyalkyl, alkoxyl, alkoxyalkyl, aminoalkyl, carboxyl, carboxyalkyl, in which carbon containing portions contain from 1 to 10 carbon atoms, and —$(CH_2)_n$—Y, where Y is a bifunctional effector molecule and n is from 0 to 6; and DTT is dithiothreitol.

$R_6$ and $R_7$ may be joined together to form a ring having from 3 to 7 members. One method of forming such a ring system is illustrated below:

Where R is a substituent selected from hydrogen, alkyl, aryl, hydroxyalkyl, aminoalkyl, carboxyl, and carboxyalkyl in which the carbon containing portions contain from 1 to 10 carbon atoms, and —$(CH_2)_n$—Y, where Y is a bifunctional effector molecule and n is from 0 to 6.

Some peptides are either resistant to disulfide reduction or undergo reduction only under harsh conditions. In such cases, it would be preferable to synthesize the corresponding linear peptide containing protected thiol groups by standard peptide synthetic methods, remove the protecting group from sulfur, and immediately carry out the condensation of the dithiol with a suitable cyclic or acyclic carbonyl compound.

Alkylation expansion, as used herein, involves inserting an alkyl moiety of from $C_2$ to $C_3$, between the two sulfur atoms. Although it is possible to insert larger alkyl moieties (greater than $C_3$) between the sulfur atoms, it is likely that the peptide's structural conformation would be significantly altered with larger alkyl moieties thereby leading to loss of bioactivity if such modifications are made. Alkylation expansion is achieved by reduction followed by alkylation of the dithiol with electrophiles or alkylating agents as follows:

where $R_8$ and $R_9$ are defined in the same manner as $R_6$ and $R_7$, above. X is a suitable leaving group such as halogen, tosyl, or mesyl groups.

$R_8$ and $R_9$ may be joined together to form a ring having from 3 to 7 members. Two methods of forming such a ring system are illustrated below:

Where R is a substituent selected from hydrogen, alkyl, aryl, hydroxyalkyl, aminoalkyl, carboxyl, and carboxyalkyl in which the carbon containing portions contain from 1 to 10 carbon atoms, and —$(CH_2)_n$—Y, where Y is a bifunctional effector molecule and n is from 0 to 6; and X is a suitable leaving group such as halogen, tosyl, or mesyl groups.

DETAILED DESCRIPTION OF THE INVENTION

The present invention provides conformationally and chemically stable analogs of cyclic bioactive peptides containing disulfide linkages. According to the present invention, the —S—S— bond is modified by one of the following techniques: (a) sulfide contraction, (b) isosteric substitution, (c) thioketal expansion, or (d) alkylation expansion. Advantageously, it is possible to couple a bifunctional effector molecule, such as a chelating agent capable of complexing diagnostically and therapeutically useful metal ions (including, for example, Tc, Re (Re-186 and Re-188), Lu, In, Ga, Co, Cu, Y (Y90), Tb, Sm, Gd, Mn, and Fe), antineoplastic agent, enzyme, coenzyme, or chemotoxin, to the disulfide bridge analogs according to the present invention.

The sulfide contraction and isosteric substitution techniques according to the present invention are illustrated by the following general formula:

Wherein $AA_1$, $AA_2$, and $AA_3$ are α-amino acids and the bonds connecting $AA_1$, Q, $AA_2$, Z, and $AA_3$ are conventional peptide bonds; k, l, and m may range from 0 to 15 with the proviso that at least two of k, l, and m are greater than zero; W and X are —S— or —CHR$_{10}$—, such that when W is —S—, then X is —CHR$_{10}$— and when W is —CHR$_{10}$—, than X is S; R$_{10}$ is —(CH$_2$)$_n$—Y; n is from 0 to 10; and Y is a reactive group capable of being coupled to a bifunctional effector molecule, such as —CO$_2$H, —NH$_2$, —OH, —N=C=O, —N=C=S, —COCl, —SO$_2$Cl, —HN—COCH$_2$— halogen, Q or Z may be the same or different and have the following general structure:

Wherein p may range from 0 to 3 and R is H, alkyl, aryl, hydroxyalkyl, alkoxyalkyl, and carboxyl wherein the carbon containing portions contain from 1 to 10 carbon atoms or the side-chain portion of naturally occurring amino acids.

The thioketal expansion and alkylation expansion techniques according to the present invention are illustrated by the following general formula:

Wherein AA$_1$, AA$_2$, AA$_3$, Q, Z, k, l, and m are the same as defined above and the bonds connecting AA$_1$, Q, AA$_2$, Z, and AA$_3$ are conventional peptide bonds. L is selected from the group consisting of Wherein the various R substituents may be the same or different and have the same definition as R, above; Y is as defined above.

Exemplary procedures for preparing the various disulfide bridge analogs according to the present invention are illustrated generally below.

Sulfide Contraction

In conventional sulfide contraction, a cysteine amino acid (which provides one of the two sulfur atoms forming the disulfide bond) is first replaced with serine. Dehydration of the serine residue gives the olefin. Finally, the Michael Reaction of the thiol onto the double bond yields the sulfide analog of the original peptide. This basic process is illustrated below with reference to the natural cyclic peptide malformin:

Sulfide analog of malformin is prepared by first synthesizing a serine-containing peptide such as one of the following peptides:

where PG is a protecting group. Second, the serine group is dehydrated to give a dehydroalanyl group.

Finally, the removal of the protecting group (PG) from sulfur followed by Michael reaction of the thiol onto the double bond in tandem yields the desired sulfide analog.

Alternatively, the sulfide derivatives can also be prepared directly by the reaction of trialkylphosphines with cyclic peptides containing disulfide linkages.

Sulfide contraction according to the present invention goes beyond what is known in the art by permitting attachment of various bifunctional molecules to one of the methylene units comprising the peptide bridge. More specifically, conventional sulfide contraction processes are modified according to the present invention by utilizing an olefinic amino acids in place of a cysteine group having the following general structure:

Wherein A$_1$ is hydrogen, alkyl, carboxyalkyl, aryl, hydroxyalkyl, in which carbon containing portions contain from 1 to 10 carbon atoms; A$_2$ and A$_3$ may be the same or different and are selected from electron withdrawing groups such as —CO$_2$R, —CO$_2$H, —CN, or —NO$_2$. The olefinic bond will serve as a Michael acceptor to receive the sulfur nucleophile. The additional —CO$_2$H, —CN or —NO$_2$ functionality will serve as a handle to attach various bifunctional effector molecules. Scheme 1, below, describes one tech- nique for preparing peptides with a sulfide contraction analog. Those skilled in the art will appreciate that similar techniques may be utilized to achieve the same cyclic peptide analogs. All of the reaction steps illustrated are well known to those skilled in the art.

Wherein EDC is ethyldimethylaminopropylcarbodiimide, DCC is dicyclohexylcarbodiimide. Other commonly used coupling methods, such as the mixed anhydride procedure described in J. Jones, *The Chemical Synthesis of Peptides*, Clarendon Press, 1991 and M. Bodanszky, *Principles of Peptide Synthesis*, 2nd Ed., Springer-Verlag, 1993 (which are incorporated herein by reference), can also be used according to the present invention.

In Scheme 1, above, a mixture of N-t-Boc-dehydroglutamic acid γ-t-butyl ester (1.1 mmol), the tetrapeptide (2) (1.0 mmol), and EDC (1.2 mmol) in DMF (5 mL) is stirred at ambient temperature for 24 hours. The reaction mixture is poured onto water and the precipitate (3) is collected by filtration, washed with water and dried. The peptide (3) is redissolved in aqueous methanol (5 mL), treated with 1 N sodium hydroxide (2.5 mL), and stirred at ambient temperature for 24 hours. Thereafter, the reaction mixture is treated with 1 N HCl (2.5 mL) and the solvent stripped off under reduced pressure. The residue is redissolved in minimum amount of water (or aqueous methanol) and purified by reverse phase flash chromatography to give the acid (4).

A method of coupling a bifunctional effector molecule (BEM) to the acid (4) follows: A mixture of the acid (4) (1.0 mmol), the imidazole ligand (shown below) (1.05 mmol), and dicyclohexylcarbodiimide (1.1 mmol) in DMF (5 mL) is stirred at ambient temperature for 24 hours.

The reaction mixture is filtered to remove dicyclohexylurea (DCU) and the filtrate poured onto water. The precipitate is collected by filtration and dried to give the fully protected peptide-ligand conjugate (5a), shown below. For compound (5a), R'' is tBu and R' is —CO$_2$tBu.

Where THP is 2-tetrahydropyranyl.

The fully protected peptide-ligand conjugate is treated with 96% formic acid (5 mL) and kept at ambient temperature for 24 hours. Formic acid is removed by evaporation in vacuo. The reaction product is redissolved in water (1 mL) and chromatographed through reverse phase (either flash or HPLC) to give the desired cyclic peptide (5b). For compound (5b), R'' and R' are —H.

Isosteric Substitution

Although isosteric substitution (replacement of a sulfur with —CH$_2$—) is known, the present invention substitutes sulfur with unit, wherein Y is a bifunctional effector molecule, that is, Y is capable of performing specific functions such as a bifunctional chelate for imaging or radiotherapeutic purposes or as a chemotoxic or antineoplastic agent for tumor chemotherapy.

Scheme 2, below, describes a technique for preparing peptides with an isosteric substitution of one of the sulfur atoms of the disulfide bridge. Those skilled in the art will appreciate that similar techniques may be utilized to achieve the same cyclic peptide analogs. All of the reaction steps illustrated are well known to those skilled in the art.

Scheme 2

Where DME is 1,2-dimethoxyethane (glyme), Boc-O-Boc is di-t-butyldicarbonate, TFA is trifluoroacetic acid, and $Et_3SiH$ is triethylsilane.

A mixture of potassium phthalimide (6) (11 mmol) and diethyl bromomalonate (7) (10 mmol) in anhydrous glyme (20 mL) was heated under reflux for 4 hours. The mixture was filtered to remove KCl and the filtrate taken to dryness under reduced pressure. The residue was purified by silica gel column chromatography to give (8).

To a mixture of (8) (10 mmol) and sodium hydride (15 mmol) in dry DMF (10 mL) is added a solution of t-butyl 4-bromocrotonate (11 mmol) in DMF (5 mL). The mixture is then heated at 55° C. to 60° C. for 2 hours and poured onto ice-cold water. The product is extracted with methylene chloride (3×25 mL), washed with water (3×50 mL), dried ($MgSO_4$), and filtered. The filtrate is taken to dryness under reduced pressure and the residue is purified by silica gel chromatography to give (9).

A mixture of (9) (10 mmol) and hydrazine hydrate (15 mmol) in methanol (20 mL) is heated under reflux for 2 hours. The solvent is removed by evaporation in vacuo and the residue is redissolved in water (25 mL) and treated with concentrated HCl (1 mL). The mixture is filtered to remove phthalhydrazide and the filtrate is treated with sodium hydroxide (22 mmol). The solution is stirred at ambient temperature for 16–20 hours, treated with concentrated HCl (2 mL) and heated at 55–60° C. for 1 hour. Water is removed under reduced pressure and the residue is purified by reverse phase flash chromatography to give t-butyl 5-amino-2-hexenedioic acid. A mixture of this amino acid (10 mmol), di-t-butyldicarbonate (Boc-O-Boc) (11 mmol) and triethylamine (11 mmol) in acetonitrile (20 mL) is stirred at ambient temperature for 24 hours. The solvent is removed under reduced pressure and the residue is dissolved in water, treated with 6 N HCl (2 mL) and flash chromatographed through reverse phase to give (10).

A mixture of the tetrapeptide (2) (1 mmol) and the acid (10) (1.05 mmol) in DMF (5 mL) is treated with EDC (1.1 mmol) and stirred at ambient temperature for 24 hours. The reaction mixture is poured onto water and the precipitate is collected by filtration, washed well with water, and dried. The solid is treated with trifluoroacetic acid (5 mL) and triethylsilane (1 mL) and kept at ambient temperature for 1 hour. TFA is removed by evaporation in vacuo. The residue is redissolved in 1 N sodium hydroxide (1 mL), filtered to remove triphenylmethane, and flash chromatographed through reverse phase to give the desired peptide (11).

Thioketal Expansion

Thioketal expansion according to the present invention involves inserting an alkylidene unit ($—CR^1R^2—$) between the two sulfur atoms. The Scheme 3, below, illustrates a technique for preparing cyclic peptides with a thioketal expansion disulfide bridge analog. Those skilled in the art will appreciate that this technique can be used with a variety of peptides containing disulfide linkages. All of the reaction steps illustrated are well known to those skilled in the art.

Scheme 3

For compound (14a): $R^1=R^2=$—H; for compound (14b): $R^1=R^2=$—$CH_3$; for compound (14c): $R^1=$—$CH_3$, $R^2=$—$(CH_2)_3CO_2H$; for compound (14d): $R^1=$—H,

Compound (14a) can be prepared, wherein $R^1$ and $R^2$ are hydrogen as follows: A solution of malformin A (1.0 mmol) in aqueous ethanol (1:1, 10 mL) is treated with sodium borohydride (1.1 mmol) and the mixture stirred at ambient temperature for 4 hours. The reaction mixture is then treated with concentrated HCl (1 mL) and the solution is taken to dryness under reduced pressure. The residue is redissolved in water (1 mL) and purified by flash chromatography over reverse phase to give (13).

A suspension of the dithiol (13) (1.0 mmol) in formaldehyde dimethyl acetal (10 mL) is treated with $BF_3 \cdot Et_2O$ (1 drop) and stirred at ambient temperature for 16 hours. The solvent is evaporated under reduced pressure and the residue treated with 1 N NaOH (1.1 mL). The solution is then flash chromatographed over reverse phase to give the desired cyclic peptide (14a).

Compound (14b) can be prepared, wherein $R^1$ and $R^2$ are —$CH_3$ substantially according to the procedure of preparing compound (14a), except that the dithiol (13) is suspended in acetone (10 mL) instead of formaldehyde dimethyl acetal.

Compound (14c) can be prepared, wherein $R^1$ is —$CH_3$ and $R^2$ is —$(CH_2)CO_2H$ as follows: A mixture of the tetrapeptide (13) (1.0 mmol) and t-butyl-5-ketohexanoate (1.1 mmol) in dioxane (10 mL) is treated with $BF_3 \cdot Et_2O$ (1 drop) and stirred at ambient temperature for 16 hours. The solvent is evaporated under reduced pressure and the residue treated with 1 N NaOH (1 mL). The solution is then flash chromatographed over reverse phase to give the desired cyclic peptide (14c).

Compound (14d) can be prepared in which $R^1=$—H, substantially according to the procedure of preparing compound (14c) except that 4-carboxybenzaldehyde is substituted for 5-ketohexanoic acid.

A bifunctional effector molecule, such as the imidazole ligand discussed above in connection with sulfide contract technique, may be coupled to compound (14d) as follows: A mixture of the acid (1.0 mmol), the imidazole ligand (shown below) (1.05 mmol), and dicyclohexylcarbodiimide (1.1 mmol) in DMF (5 mL) is stirred at ambient temperature for 24 hours.

The reaction mixture is filtered to remove dicyclohexylurea (DCU) and the filtrate poured onto water. The precipitate is collected by filtration and dried to give the peptide-ligand conjugate (14d), shown below.

The cyclic peptides resulting from thioketal expansion described herein may retain bioactivity and may be useful in some therapeutic application, even if they do not contain additional bifunctional effector molecules. The effector molecules are introduced for targeted delivery of radio-nuclides for imaging or radiotherapeutic purposes and chemotoxic or antineoplastic agents for chemotherapy in cases where the peptide alone cannot provide the desired therapeutic effect. That is, in those cases where receptor binding occurs, but the desired therapeutic physiologic effect is not observed.

Alkylation Expansion

Alkylation expansion, as used herein, involves inserting an alkyl moiety of from $C_2$ to $C_3$, between the two sulfur atoms. Longer alkyl chains can be introduced; however, the probability of preserving the topological similarity between the original peptide and the modified analog may be significantly reduced with large units. Alkylation expansion is achieved by reduction, as in thioketal expansion above, followed by alkylation. The Scheme 4, below, illustrates a technique for preparing cyclic peptides with an alkylation expansion disulfide bridge analog. Those skilled in the art will appreciate that this technique can be used with a variety of peptides containing disulfide linkages. All of the reaction steps illustrated are well known to those skilled in the art.

Scheme 4

15

A solution of (13) (1 mmol) in water (5 mL) and sodium bicarbonate (3 mmol) is treated with methyl 2-bromomethyl acrylate (1.1 mmol) and the entire mixture is stirred at ambient temperature for 24 hours. Thereafter, 1 N NaOH (1 mL) is added to the mixture and stirred at ambient temperature for 24 hours. The reaction mixture is treated with 1 N HCl (3.2 mL) and concentrated to about half the original volume. The solution is then flash chromatographed over reverse phase to give the desired cyclic peptide (15).

Although the foregoing discussion has illustrated the present invention in the context of the cyclic peptide malformin A, it will be appreciated by those skilled in the art that the teachings of the present invention may be adapted for use in other small peptides containing disulfide linkages. For example, several well known peptides such as octreotide, [D-Pen$^{2,5}$,p-Cl—Phe$^4$]-Enkephalin, [D-Pen$^{2,5}$]-Enkephalin, oxytocin, and other known and novel cyclic peptides may be used in the process of the present invention. In addition, longer fragments derived from the structures of the "C×C" family of chemotactic cytokines (or "chemokines") or to "CC" family of chemokines can also be used.

These two families are chemoattractant for neutrophils and monocytes respectively and are derived from genes resident on chromosomes 4(C×C) and 17(CC). The C×C and CC designations denote a structural feature of these families wherein two cysteines may or may not be separated by a variable amino acid, X. It is important to note however, that these adjacent or closely spaced cysteines are not disulfide bonded to one another. Rather, they are bonded to other cysteines further down the molecule to fold the molecule into one which characteristically contains three beta sheets and an alpha helix. For example in IL-8, the cysteine at position 7 is bonded to a cysteine at position 34 and the one at position 9 is bonded to a cysteine at position 50. The residues at 7 and 9 are not disulfide bonded to one another in the native molecule.

The C×C family of chemotactic cytokines includes, but is not limited to, Interleukin-8, Macrophage Inflammatory Protein-2 (MIP-2), Growth Regulated Gene Products (GRO) including GRO$_\alpha$, GRO$_\beta$, and GRO$_\gamma$, Melanoma Growth Simulating Activity (MGSA), Platelet Factor-4 (PF-4), Gamma-interferon Inducible Protein (gamma-IP), Platelet Basic Protein, Connective Tissue Activating Protein (CTAP-III), Beta-thromboglobulin (β-TG), Neutrophil-activating Peptide-2 (NAP-2), Chicken v-src-inducible Protein (93), Epithelial Cell-Derived Neutrophil-Activating Factor-78 (ENA-78), and the related peptides described in U.S. Pat. No. 5,079,228 which is incorporated herein by reference.

Typical CC chemokines include, but are not limited to, Chemoattractant Protein (MCP) material, such as Monocyte Chemoattractant Protein-1 (MCP-1), MIP$_\alpha$, MIP$_\beta$, RANTES, I-309, MCP-2 (also known as HC14), and MCP-3.

It can readily be appreciated that the methods of the current invention can be applied to the construction of fragments derived from the structure of the C×C and CC chemokines wherein the closely adjacent CC residues (rather than the more remote residues that are bonded in the native molecule) are used to incorporate the ligands described herein.

Cyclic Peptide Analog Chemical Stability

Those skilled in the art will appreciate that each of the foregoing methods of preparing cyclic peptide analogs converts a disulfide linkage into one or more thioether moieties. Thioethers are well known to be chemically stable under conditions where disulfides are unstable.

Cyclic Peptide Analog Conformational Similarity

Molecular modeling studies have been conducted comparing octreotide (16), a cyclic octapeptide containing a disulfide linkage, and its corresponding thioketal analog (17).

Figure 1:
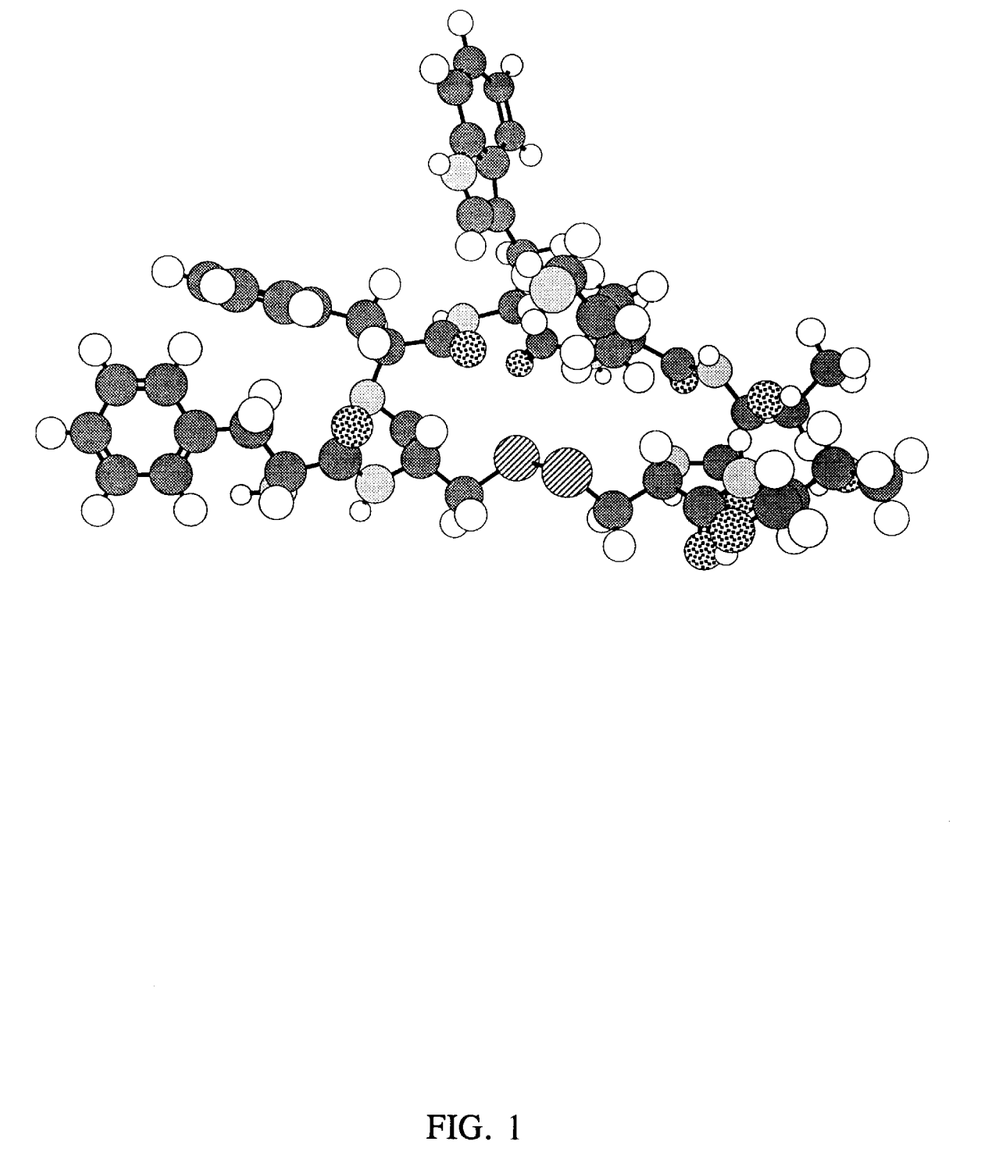
FIG. 1 is a three dimensional representation of the somatostatin receptor binding peptide, octreotide.
Figure 2:
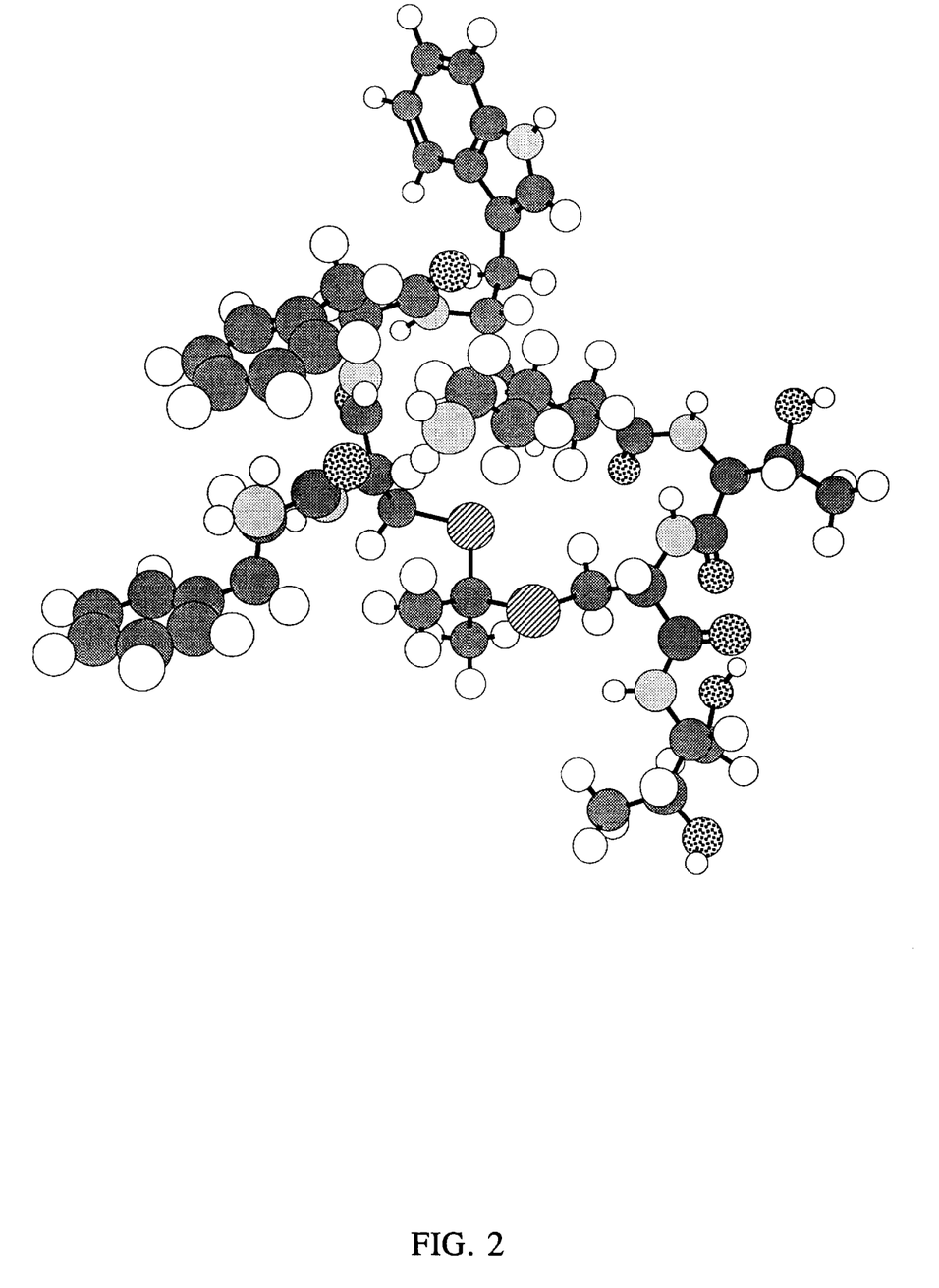
FIG. 2 is a three dimensional representation of a thioketal analog of octreotide.

As shown in structures depicted in FIGS. 1 and 2, there is a striking 3-dimensional topological similarity between the structures. Molecular modeling with other cyclic peptides according to the present invention showed very close topological similarity between the original and modified cyclic peptides.

From the foregoing, it will be appreciated that the present invention provides analogs of cyclic peptides containing disulfide linkages which have improved chemical and biological stability while substantially retaining the overall 3-dimensional peptide conformation. The present invention further provides cyclic peptide analogs having a bifunctional effector molecule coupled thereto.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The claimed invention is:

1. A cyclic peptide analog having the following general formula:

wherein $(AA_1)_k$, $(AA_2)_l$, and $(AA_3)_m$ are α-amino acids in the peptide and the bonds connecting $(AA_1)_k$, Q, $(AA_2)_l$, Z, and $(AA_3)_m$ are conventional peptide bonds; k, l, and m are the number of α-amino acids and may range from 0 to 15 with the proviso that at least two of k, l, and m are greater the zero; W and X are —S— or —CHR$^1$—, such that when W is —S—, then X is —CHR$^1$— and when W is —CHR$^1$—, then X is —S—; R$^1$ is —(CH$_2$)$_n$—Y; n is from 0 to 10; Y is a reactive functional group capable of being coupled to a bifunctional effector molecule; and Q and Z may be the same or different and have the following general structure:

wherein p may range from 0 to 3 and $R^2$ is H, alkyl, aryl, hydroxyalkyl, alkoxyalkyl, and carboxyl wherein the carbon containing portions contain from 1 to 10 carbon atoms or the side chain portion of naturally occurring α-amino acids.

2. A cyclic peptide analog as defined in claim 1, wherein Y is selected from group of —$CO_2H$, —$NH_2$, —OH, —N=C=O, —N=C=S, —COCl, —$SO_2Cl$, —HN—$COCH_2$-halogen, 3. A cyclic peptide analog as defined in claim 1, further comprising a bifunctional effector molecule bound to functional group Y.

4. A cyclic peptide analog as defined in claim 3, wherein $(AA_1)_k$, Q, $(AA_2)_l$, Z, and $(AA_3)_m$ collectively form the amino acid sequence of octreotide.

5. A cyclic peptide analog as defined in claim 4, wherein the bifunctional effector molecule is a bifunctional chelating agent capable of complexing a metal selected from Tc, Re, In, Ga, Co, Cu, Y, Lu, Tb, Sm, Gd, Mn, and Fe.

6. A cyclic peptide analog having the following general formula:

wherein $(AA_1)_k$, $(AA_2)_l$, and $(AA_3)_m$ are α-amino acids in the peptide and the bonds connecting $(AA_1)_k$, Q, $(AA_2)_l$, Z, and $(AA_3)_m$ are conventional peptide bonds; k, l, and m are the number of α-amino acids and may range from 0 to 15, with the proviso that at least two of k, l, and m are greater than zero; Q and Z may be the same or different and have the following general structure:

wherein p may range from 0 to 3 and R is H, alkyl, aryl, hydroxyalkyl, alkoxyalkyl, and carboxyl wherein the carbon containing portions contain from 1 to 10 carbon atoms or the side chain portion of naturally occurring α-amino acids; L is selected from the group consisting of wherein the various R substituents may be the same or different and have the same definition as R, above; and Y is a functional group capable of being coupled to a bifunctional effector molecule.

7. A cyclic peptide analog as defined in claim 6, wherein Y is selected from group of —$CO_2H$, —$NH_2$, —OH, —N=C=O, —N=C=S, —COCl, —$SO_2Cl$, —HN—$COCH_2$-halogen, 8. A cyclic peptide analog as defined in claim 6, further comprising a bifunctional effector molecule bound to functional group Y.

9. A cyclic peptide analog as defined in claim 6, wherein $(AA_1)_k$, Q, $(AA_2)_l$, Z, and $(AA_3)_m$ collectively form the amino acid sequence of octreotide.

10. A cyclic peptide analog as defined in claim 9, wherein the bifunctional effector molecule is a bifunctional chelating agent capable of complexing a metal selected from Tc, Re, In, Ga, Co, Cu, Y, Lu, Tb, Sm, Gd, Mn, and Fe.

* * * * *